(12) United States Patent
Zhou et al.

(10) Patent No.: US 9,452,232 B2
(45) Date of Patent: Sep. 27, 2016

(54) STERILIZABLE ASSEMBLED BRACKET FOR ASEPTIC TECHNIQUE EXPERIMENTS

(71) Applicant: HEBEI UNIVERSITY OF SCIENCE AND TECHNOLOGY, Shijiazhuang (CN)

(72) Inventors: Xiaohui Zhou, Shijiazhuang (CN); Le Xu, Shijiazhuang (CN); Jun Liu, Shijiazhuang (CN); Hao Liu, Shijiazhuang (CN)

(73) Assignee: HEBEI UNIVERSITY OF SCIENCE AND TECHNOLOGY, Shijiazhuang (CN)

( * ) Notice: Subject to any disclaimer, the term of this patent is extended or adjusted under 35 U.S.C. 154(b) by 0 days.

(21) Appl. No.: 14/830,736

(22) Filed: Aug. 20, 2015

(65) Prior Publication Data

US 2015/0352239 A1    Dec. 10, 2015

Related U.S. Application Data

(63) Continuation of application No. PCT/CN2014/081583, filed on Jul. 3, 2014.

(30) Foreign Application Priority Data

Jul. 25, 2013 (CN) .......................... 2013 1 0316906

(51) Int. Cl.
*A61L 2/26* (2006.01)
*B01L 9/00* (2006.01)
*C12M 3/00* (2006.01)
*C12M 1/00* (2006.01)
*C12M 1/12* (2006.01)
*B01L 9/06* (2006.01)

(52) U.S. Cl.
CPC .. *A61L 2/26* (2013.01); *B01L 9/00* (2013.01); *C12M 23/48* (2013.01); *C12M 29/00* (2013.01); *C12M 37/00* (2013.01); *B01L 9/06* (2013.01)

(58) Field of Classification Search
CPC .......... A61L 2/26; B01L 9/00; C12M 23/48; C12M 29/00; C12M 37/00
USPC ......................................................... 422/566
See application file for complete search history.

(56) References Cited

U.S. PATENT DOCUMENTS 4,115,200 A * 9/1978 Anderson .............. C12M 23/12
141/237
4,497,227 A * 2/1985 Stasiek ................. B25B 13/465
192/43.2

(Continued)

FOREIGN PATENT DOCUMENTS

CN        201161198      * 12/2008
CN        201161198 Y    12/2008

(Continued)

*Primary Examiner* — Sean E Conley
*Assistant Examiner* — Jacqueline Brazin
(74) *Attorney, Agent, or Firm* — Perkins Coie LLP

(57) ABSTRACT

An assembled sterilization rack for sterile experiment relates to supporting devices used in experiment involving culture of microorganisms and/or cells. The rack includes a lateral frame, retaining wires, connectors, a base frame, heat resistant rods, connecting rings, a temperature-displaying control unit, and N temperature sensors. The lateral frame and the base frame are connected through the connectors. The lateral frame and the base frame have their surfaces facing each other provided with a plurality of retaining wires. The rods have two ends mounted on the symmetrically arranged retaining wires, respectively. The base frame has its upper surface provided with a plurality of connecting rings. The rods have the two ends received in the symmetrically arranged connecting rings, respectively. The temperature sensors are connected with the temperature-displaying control unit. In cell culture experiment, this invention can be applied to support elements used for vertical culture of cells in rectangular culture dishes.

15 Claims, 2 Drawing Sheets

(56) References Cited

U.S. PATENT DOCUMENTS 4,854,475 A * 8/1989 Riihimaki ............. A61L 2/26
                                                    206/369
2013/0298735 A1* 11/2013 Hobden ............. B25B 13/465
                                                    81/60

FOREIGN PATENT DOCUMENTS

| CN | 202290112 | * | 7/2012 |
| CN | 202590821 U | | 12/2012 |
| CN | 203204463 | * | 9/2013 |
| CN | 103343087 A | | 10/2013 |

* cited by examiner

STERILIZABLE ASSEMBLED BRACKET FOR ASEPTIC TECHNIQUE EXPERIMENTS

CROSS REFERENCE TO RELATED APPLICATIONS

This application is a continuation of PCT/CN2014/081583, filed 2014 Jul. 3, which claims priority to CN 201310316906.X filed 2013 Jul. 25, both of which are incorporated herein by reference.

TECHNICAL FIELD

The present invention relates to supporting devices used in experiments involving culture of microorganisms and/or cells.

DESCRIPTION OF RELATED ART

Currently, inoculation loops and applicators prepared for sterile experiment on a clean bench are placed directly on the bench surface and are later sterilized by open flame from an alcohol burner before use. After such dry heat sterilization, the sterilized tools have to be held in operators' hands until they become cool, and this causes great inconvenience during the experiment. Particularly, for experiment where different bacteria have to be incubated or different plates have to be prepared, the loops and/or applicators need open-flame dry heat sterilization after each time of use, and this is quite time-consuming. Moreover, the temperatures of the processed inoculation loops and/or applicators and of culture medium that has been sterilized in steam are measured only relying on operators' experience. Once such empirical determination is faulty, the result of the experiment can be adversely affected, in turn highly risking the efficiency of the experiment. Moreover, there have not been useful supporting racks designed for vertical culture of rectangular culture dishes in incubators.

SUMMARY OF THE INVENTION

One objective of the present invention is to provide an assembled sterilization rack for sterile experiment that eliminates the problems in the prior art that during experiment the operators have to hold inoculation loops and/or applicators sterilized by open flame in hands for cooling and that the merely empirically determined temperature of culture medium sterilized by steam might be inaccurate and in turn adversely affects the accuracy of the experimental results.

The assembled sterilization rack for sterile experiment comprises a lateral frame, retaining wires, connectors, a base frame, heat resistant rods each having a plurality of semicircular positioning elements, connecting rings, a temperature-displaying control unit, and N temperature sensors, where N is an integer greater than or equal to one. The lateral frame and the base frame are dimensionally identical U-shaped frames. The lateral frame and the base frame are connected through the connectors. Arms of the U-shaped frame of the lateral frame are symmetrically provided with a plurality of retaining wires. The heat resistant rods are horizontally mounted on the retaining wires. Arms of the U-shaped frame of the base frame are symmetrically provided with a plurality of connecting rings. The heat resistant rods fixed to the connecting ring are parallel to the heat resistant rods on the lateral frame. The N temperature sensors are arranged at N temperature-measured sites, respectively. The N temperature sensors have output ends for outputting temperature-sensing signals connected with input ends of the temperature-displaying control unit for inputting N temperature-sensing signals.

The present invention features for the heat resistant rods that are arranged on the lateral frame and the base frame and have the positioning rings, and also features for the angular adjustability between the base frame and the lateral frame, so that inoculation loops and/or applicators can be placed between the positioning elements of the lateral frame and the positioning elements of the base frame. The disclosed rack is structurally simple and angularly adjustable and can be assembled according to its use. With the temperature sensors that measure temperatures data in a real-time manner and with the temperature-displaying control unit that displays the measured temperatures, experiment can be significantly improved in terms of accuracy and efficiency.

DETAILED DESCRIPTION OF THE INVENTION

Figure 1:
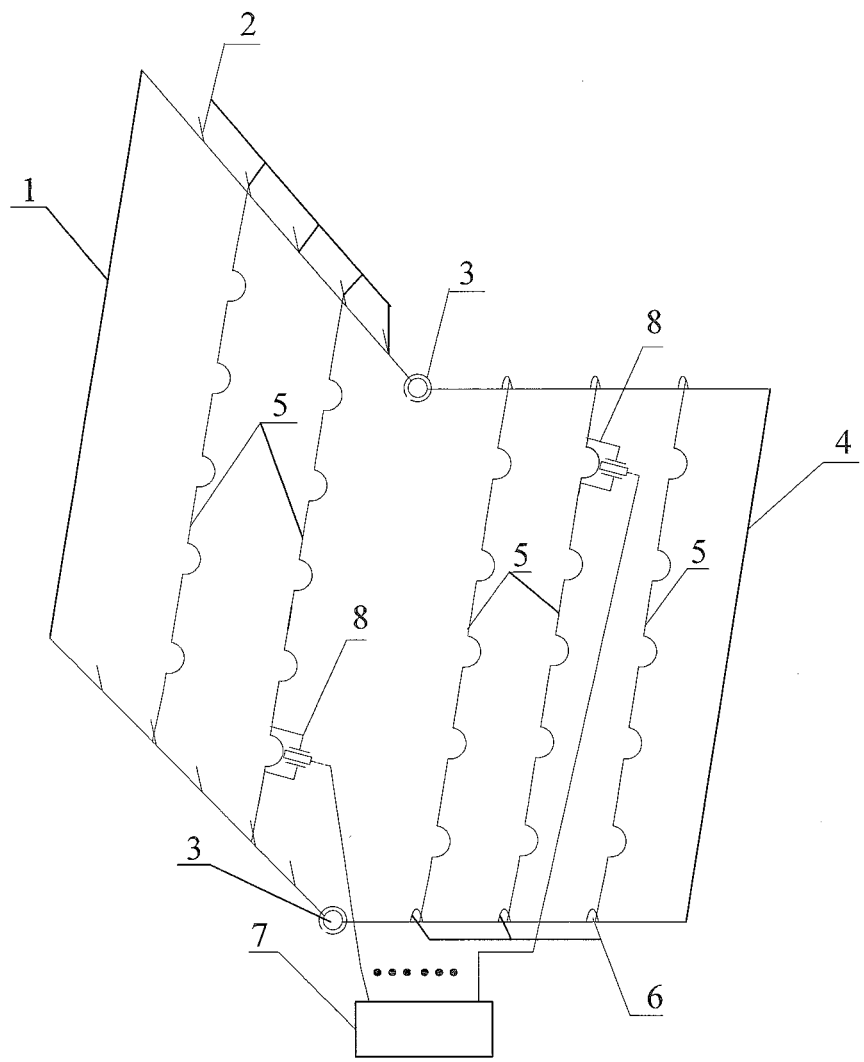
FIG. 1 is a structurally schematic drawing depicting an assembled sterilization rack for sterile experiment according to the present invention.

In a first embodiment, with reference to FIG. 1, an assembled sterilization rack for sterile experiment according to the present embodiment comprises a lateral frame 1, retaining wires 2, connectors 3, a base frame 4, heat resistant rods 5 each having a plurality of semicircular positioning elements, connecting rings 6, a temperature-displaying control unit 7, and N temperature sensors 8, where N is an integer greater than or equal to one. The lateral frame 1 and the base frame 4 are dimensionally identical U-shaped frames. The lateral frame 1 and the base frame 4 are connected through the connectors 3. Arms of the U-shaped frame of the lateral frame 1 are symmetrically provided with a plurality of retaining wires 2. The heat resistant rods 5 are horizontally mounted on the retaining wires 2. Arms of the U-shaped frame of the base frame 4 are symmetrically provided with a plurality of connecting rings 6. The heat resistant rods 5 fixed to the connecting ring 6 are parallel to the heat resistant rods 5 on the lateral frame 1. The N temperature sensors 8 are arranged at N temperature-measured sites, respectively, and have output ends for outputting temperature-sensing signals connected with input ends of the temperature-displaying control unit 7 for inputting the N temperature-sensing signals.

In the present embodiment, the heat resistant rods may be made of metal, and made of platinum. The metal heat resistant rods have good heat conduction so as to allow fast cooling of the inoculation loops and/or applicators.

Figure 2:
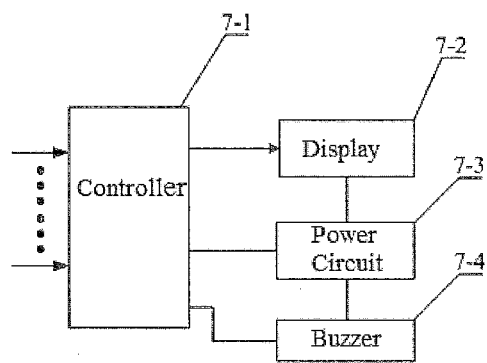
FIG. 2 is a block diagram structurally showing a temperature-displaying control unit of the assembled sterilization rack according to a second embodiment.

In a second embodiment, with reference to FIG. 2, the second embodiment further delimits the assembled sterilization rack for sterile experiment disclosed in the first embodiment. Here, the temperature-displaying control unit 7 comprises a controller 7-1, a display 7-2, a power circuit 7-3, and a buzzer 7-4. A power output end of the power circuit 7-3 connects with a power input end of the controller 7-1, a power input end of the display 7-2, and a power input end of the buzzer 7-4, respectively. Input ends of the controller 7-1 for inputting the N temperature-sensing signals connects with output ends of the N temperature sensors 8 for outputting the sensing signals. An output end of the controller 7-1 for outputting a displaying signal connects with an input end of the display 7-2 for inputting the displaying signals. An output end of the controller 7-1 for outputting a buzzer-activating control signal connects with an input end of the buzzer 7-4 for inputting the buzzer-activating control signal.

In a third embodiment, with reference to FIG. 2, the third embodiment further delimits the assembled sterilization rack for sterile experiment disclosed in the second embodiment. The controller 7-1 is realized by using a single-chip microcontroller.

In a fourth embodiment, with reference to FIG. 1, the fourth embodiment further delimits the assembled sterilization rack for a sterile experiment disclosed in the first embodiment. Here, the positioning elements are evenly distributed over the heat resistant rods 5.

In a fifth embodiment, with reference to FIG. 1, the fifth embodiment further delimits the assembled sterilization rack for sterile experiment disclosed in the first embodiment. Here, the lateral frame 1 and the base frame 4 are both formed by heat resistant frames.

Figure 3:
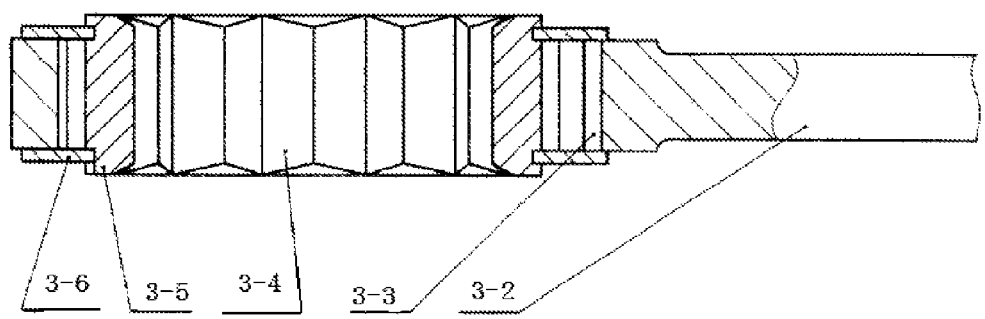
FIG. 3 is cross-sectional view of a reversible ratchet mechanism in a connector 3 of the assembled sterilization rack according to a sixth embodiment.
Figure 4:
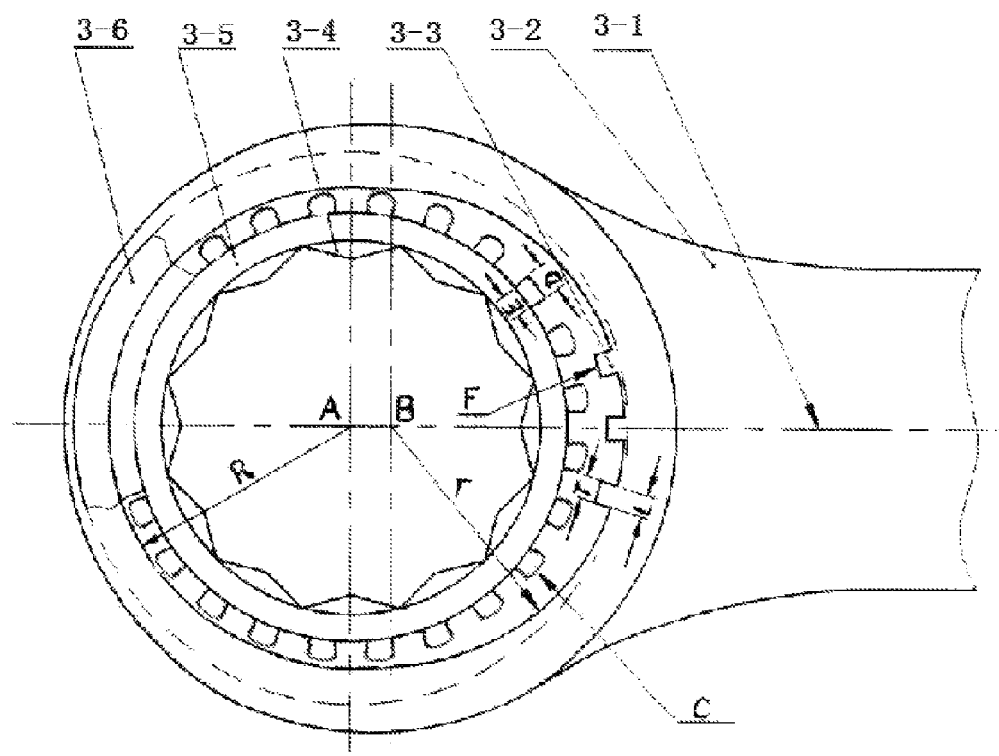
FIG. 4 is a plan view of the reversible ratchet mechanism in the connector 3 of the assembled sterilization rack according to the sixth embodiment.

In a sixth embodiment, with reference to FIG. 3 and FIG. 4, the sixth embodiment further delimits the assembled sterilization rack for sterile experiment disclosed in the first embodiment. Here, the connector 3 has a reversible ratchet mechanism.

The connectors 3 have a through hole that has two coplanar circle centers A, B. Up to twenty internal teeth 3-3 are formed on a wall of the through hole symmetrically against a point that is an intersection point of an imaginary connecting line linking the circle centers A, B and one site R or r on the wall of the through hole. A ratchet 3-5 that has an outer wall peripherally formed with a row of teeth is received in the through hole. The ratchet 3-5 is configured to radially move to and fro toward either of the circle centers A and B. The teeth of the ratchet 3-5 can engage with each of the internal teeth 3-3, so as to radially rotate in either direction as a whole or to rotate independently of each other. A handle 3-2 extends radially outward from an outer periphery of the through hole. The middle line of the handle 3-2 is a center line 3-1. The center line 3-1 coincides with, is parallel to, or intersects the imaginary connecting line linking the circle centers A and B. The ratchet 3-5 is provided with a nut-fitting hole, a square insert, or a mechanical workpiece 3-4. Each of the teeth of the ratchet 3-5 has a curved top surface C and has a top width D equal to or greater than a root width E. Each of the internal teeth 3-3 has a curved or flat top surface F and has a top width T equal to or greater than a root width L. The outer periphery of the opposite ends of the ratchet 3-5 has two retaining rings 3-6 for retaining the ratchet 3-5 in the through hole and two recesses for receiving the retaining rings 3-6. The retaining rings 3-6 are spring loops cut at a radius thereof.

In use, by radially pushing the handle 3-2 slightly and bringing the internal teeth 3-3 near the handle 3-2 engaged with the teeth of the ratchet 3-5, the assembled sterilization rack can be radially rotated and thus expanded. On the other hand, by radially pulling the handle 3-2 slightly, the internal teeth 3-3 are disengaged from the teeth of the ratchet 3-5 so that the handle 3-2 is allowed to be rotated reversely to collapse the assembled sterilization rack.

The present invention features for the heat resistant rods that are arranged on the lateral frame and the base frame and have the positioning elements, and also features for the angular adjustability between the base frame and the lateral frame, so that different needs of experiments can be met. The connector uses a reversible ratchet mechanism not only to control the open angle formed by the base frame and the lateral frame, so that the rack can be posed with the open angle as an obtuse angle, a right angle, or an acute angle, but also the lateral frame can be well positioned and supported. The lateral frame has the retaining wires for propping up the heat resistant rods that are equipped with multiple positioning elements. In use, an inoculation loop or applicator can be placed between an upper positioning element and a lower positioning element. The sensors may be arranged at different sites on the rack for sensing the temperatures of heated culture medium or flamed experimental tools such as inoculation loops and applicators. When a sterilized container for culture medium is placed on the temperature sensor, the temperature-displaying control unit can display the temperature of the culture medium, and the buzzer buzzes when this temperature reaches a value required by the ongoing experiment, thereby helping to prevent a solid-culture-medium pour plate, where it is used, from being overheated or overcooled. The temperatures of flamed inoculation loops and/or applicators sensed by the temperature sensors can be read out at the display, thereby eliminating the risk of overheated inoculation that impedes the growth of the planted microorganisms.

The advancement of the present invention includes: (1) reasonable design because the disclosed rack is structurally simple and angularly adjustable and can be assembled according to its use; (2) extensive use because the disclosed rack can well support various tools such as inoculation loops and/or applicators that are sterilized by open flame, and can be used as a support for vertical culture in rectangular culture dishes, while the disclosed rack can sense temperatures of experiment devices such as inoculation loops, applicators and Erlenmeyer flasks; (3) professional practicability because the disclosed rack is heat resistant and can withstand autoclaving, thus being perfect for sterile experiment performed on culture of microorganisms and cells; and (4) value-added functions provided by the temperature sensors and the warning from the buzzer, which help to reduce faults in experiments, thereby improving test efficiency.

What is claimed is:

1. An assembled sterilization rack for a sterile experiment, comprising
 a lateral frame and a base frame, of which an angle therebetween is adjustable, wherein the lateral frame and the base frame respectively has at least one heat resistant rod having a plurality of positioning elements disposed thereon for placing experiment devices and positioning the experiment devices in the positioning elements, wherein at least one temperature sensor is arranged on at least one temperature-measured site senses temperatures of the experiment devices and transmits the temperatures to a temperature-displaying control unit connected to the at least one temperature sensor for indicating the temperatures,
 wherein the lateral frame and the base frame are U-shaped frames of identical length, and are connected through connectors,
 wherein the connectors include a reversible ratchet mechanism, wherein the connector has a through hole formed by two coplanar arcs whose circle centers are A and B, wherein internal teeth are symmetrically formed on a wall of the through hole, wherein a ratchet that has an outer wall peripherally formed with a row of teeth is received in the trough hole, and the ratchet is configured to radially move to and fro toward either of the circle centers A and B, and wherein the teeth of the ratchet can engage with each of the internal teeth.

2. The assembled sterilization rack for sterile experiment of claim 1, wherein the positioning elements are temperature-measured sites, the temperature sensors are correspondingly arranged at the positioning elements.

3. The assembled sterilization rack for sterile experiment of claim 2, wherein the positioning elements are semicircular positioning elements and evenly distributed over the heat resistant rods.

4. An assembled sterilization rack for a sterile experiment of claim 1, wherein arms of U-shaped frame of the lateral frame are symmetrically provided with a plurality of retaining wires for horizontally mounting the heat resistant rods,
wherein arms of U-shaped frame of the base frame are symmetrically provided with a plurality of connecting rings for positioning the heat resistant rods,
wherein the at least one heat resistant rod on the base frame is parallel to the at least one heat resistant rod on the lateral frame.

5. The assembled sterilization rack for sterile experiment of claim 1, wherein the lateral frame and the base frame are dimensionally identical U-shaped frames.

6. The assembled sterilization rack for a sterile experiment of claim 1, wherein a handle extends radially outward from an outer periphery of the through hole, the middle line of the handle is a center line of the handle, wherein the center line of the handle coincides with, is parallel to, or intersects an imaginary connecting line linking the circle centers A and B.

7. The assembled sterilization rack for sterile experiment of claim 6, wherein the ratchet is provided with a nut-fitting hole, a square insert, or a mechanical workpiece.

8. The assembled sterilization rack for sterile experiment of claim 7, wherein each of the teeth of the ratchet has a curved top surface C and has a top width D equal to or greater than its root width E; wherein each of the internal teeth has a curved or flat top surface F and has a top width T equal to or greater than its root width L.

9. The assembled sterilization rack for sterile experiment of claim 1, wherein the heat resistant rods are heat resistant rods made of metal, and heat resistant rods made of platinum.

10. The assembled sterilization rack for sterile experiment of claim 1, wherein the temperature-displaying control unit comprises:
a controller receiving temperature-sensing signals from the temperature sensors and transmitting temperature-displaying signals and buzzer-activating control signals;
a display receiving temperature-displaying signals from the controller;
a buzzer receiving buzzer-activating control signals from the controller, and buzzing based on the buzzer-activating control signals;
a power circuit supplying power separately for the controller, the display and the buzzer.

11. The assembled sterilization rack for sterile experiment of claim 10, wherein a power output of the power circuit connects with a power input end of the controller, a power input end of the display, and a power input end of the buzzer, respectively, wherein an input end of the controller for inputting the at least one temperature-sensing signal connects with an output end of the at least one temperature sensor for outputting the sensing signals, wherein an output end of the controller for outputting the displaying signals connects with an input end of the display for inputting the displaying signals, and wherein an output end of the controller for outputting the buzzer-activating control signals connects with an input end of the buzzer for inputting the buzzer-activating control signals.

12. The assembled sterilization rack for sterile experiment of claim 10, wherein the controller is a single-chip microcontroller.

13. An assembled sterilization rack for sterile experiment, characterized in that, the assembled sterilization rack comprising a lateral frame, retaining wires, connectors, a base frame, heat resistant rods each having a plurality of semicircular positioning elements, connecting rings, a temperature-displaying control unit, and N temperature sensors, where N is an integer greater than or equal to one, wherein the lateral frame and the base frame are U-shaped frames that are dimensionally identical to each other, the lateral frame and the base frame are connected through the connectors, wherein arms of the U-shaped frame of the lateral frame are provided symmetrically with a plurality of retaining wires, wherein the heat resistant rods are horizontally mounted on the retaining wires, wherein arms of the U-shaped frame of the base frame are provided symmetrically with a plurality of connecting rings, the heat resistant rods fixed to the connecting rings are parallel to the heat resistant rods on the lateral frame, wherein the N temperature sensors are arranged at N temperature-measured sites, respectively, the N temperature sensors have output ends for outputting temperature-sensing signals connected with input ends of the temperature-displaying control unit for inputting N temperature-sensing signals;
the temperature-displaying control unit including a controller, a display, a power circuit and a buzzer, wherein a power output end of the power circuit connects with a power input end of the controller, a power input end of the display, and a power input end of the buzzer, respectively, wherein input ends of the controller for inputting the N temperature-sensing signals connect with output ends of the N temperature sensors for outputting the sensing signals, wherein an output end of the controller for outputting a displaying signal connects with an input end of the display for inputting the displaying signals, and wherein an output end of the controller for outputting a buzzer-activating control signal connects with an input end of the buzzer for inputting the buzzer-activating control signal; and
wherein the lateral frame and the base frame are both formed by heat resistant frames; wherein the heat resistant rods are heat resistant rods made of metal; wherein the connectors are formed as a reversible ratchet mechanism; wherein the connectors each have a through hole formed by two coplanar arcs whose circle centers are A and B, wherein up to twenty internal teeth are formed around a wall of the through hole symmetrically about an imaginary connecting line linking the circle centers A and B, wherein a ratchet that has an outer wall peripherally formed with a row of teeth is received in the through hole, and the ratchet is configured to radially move to and fro toward either of the circle centers A and B, wherein the teeth of the ratchet can engage with each of the internal teeth, so as to radially rotate in either direction as a whole or to rotate independently of each other; a handle extends radially outward from an outer periphery of the through hole, the middle line of the handle is a center line of the handle, the center line of the handle coincides with, is parallel to, or intersects the imaginary connecting line linking the circle centers A and B; wherein the ratchet is provided with a nut-fitting hole, a square insert, or a mechanical workpiece; wherein each of the teeth of the ratchet has a curved top surface C and has a top width D equal to or greater than its root width E; wherein each of the internal teeth has a curved or flat top surface F and has a top width T equal to or greater than its root width L; the outer periphery of the opposite ends of the ratchet has two retaining rings for retaining the ratchet in the through hole and two recesses for receiving the retaining rings; by radially pushing the handle slightly, the internal teeth near the handle come to engage with the teeth of the ratchet, so the assembled sterilization rack is allowed to be rotationally expanded; and by radially pulling the handle slightly, the internal teeth separate from the teeth of the ratchet, so that the handle is allowed to be rotated to collapse the assembled sterilization rack.

14. The assembled sterilization rack of claim 13, wherein the controller is a single-chip microcontroller.

15. The assembled sterilization rack of claim 13, wherein the positioning elements are evenly distributed over the heat resistant rods.

* * * * *